(12) United States Patent
Martin

(10) Patent No.: US 8,944,878 B2
(45) Date of Patent: Feb. 3, 2015

(54) ARTIFICIAL EYE AND METHOD OF MANUFACTURE

(75) Inventor: Roger A. Martin, Albemarle, NC (US)

(73) Assignee: McKenzie Sports Products, LLC, Salisbury, NC (US)

(*) Notice: Subject to any disclaimer, the term of this patent is extended or adjusted under 35 U.S.C. 154(b) by 416 days.

(21) Appl. No.: 12/884,571

(22) Filed: Sep. 17, 2010

(65) Prior Publication Data

US 2012/0071971 A1    Mar. 22, 2012

(51) Int. Cl.
    *A63H 3/38*    (2006.01)
    *A61F 2/14*    (2006.01)
    *G09B 23/30*   (2006.01)
    *G09B 23/36*   (2006.01)

(52) U.S. Cl.
    CPC .............. *A61F 2/141* (2013.01); *G09B 23/30* (2013.01); *G09B 23/36* (2013.01); *A61F 2250/0081* (2013.01)
    USPC ........................... 446/392; 446/389; 434/296

(58) Field of Classification Search
    USPC ............................ 446/389, 392; 434/271, 296
    See application file for complete search history.

(56) References Cited

U.S. PATENT DOCUMENTS

| | | | | |
|---|---|---|---|---|
| 1,763,312 A | | 6/1930 | Marcus | |
| 1,979,321 A | * | 11/1934 | Brooklyn | 446/219 |
| 3,092,931 A | * | 6/1963 | Samo | 446/389 |
| 3,286,394 A | * | 11/1966 | Brudney | 446/389 |
| 3,372,493 A | * | 3/1968 | Birch | 434/84 |
| 3,590,521 A | * | 7/1971 | Samo | 446/343 |
| 4,477,500 A | * | 10/1984 | Powell | 428/16 |
| 4,601,673 A | * | 7/1986 | Nasca | 446/389 |
| 4,637,159 A | * | 1/1987 | Kulis | 43/42.32 |
| 4,642,209 A | | 2/1987 | Powell | |
| 5,645,780 A | | 7/1997 | Rinehart | |
| 5,735,895 A | | 4/1998 | Rinehart | |
| 6,099,379 A | | 8/2000 | Eppley | |
| 6,824,267 B2 | | 11/2004 | Streibig | |
| 7,198,539 B2 | | 4/2007 | Lam et al. | |
| 7,503,827 B2 | | 3/2009 | Alfaro | |
| 2007/0190510 A1 | | 8/2007 | Johnson | |
| 2008/0090015 A1 | | 4/2008 | Alfaro | |

OTHER PUBLICATIONS

Van Dyke's, Van Dyke's Custom Eyes, http://www.vandykestaxidermy.com/van-dyke-s-custom-eyes.html, Jun. 15, 2010, 1 page.
Nia's Tiny Wonders, YouTube, Making Tiny Glass Like Eyes, http://www.youtube.com/watch?v=nr1PdfHssO0, Jun. 15, 2010.

* cited by examiner

*Primary Examiner* — Gene Kim
*Assistant Examiner* — Joseph B Baldori
(74) *Attorney, Agent, or Firm* — Moore & Van Allen PLLC; Nicholas C. Russell

(57) ABSTRACT

An artificial eye comprises a transparent cup-shaped body member having a substantially concave inner surface and a substantially convex outer surface. The body member includes a pupil portion at the center, a substantially annular iris portion abutting the peripheral edge of the pupil portion for defining a boundary between the pupil portion and the iris portion, and at least one groove formed in the concave inner surface of the iris portion of the body member. The grooves are visible through the iris portion for reflecting light through the body member.

10 Claims, 3 Drawing Sheets

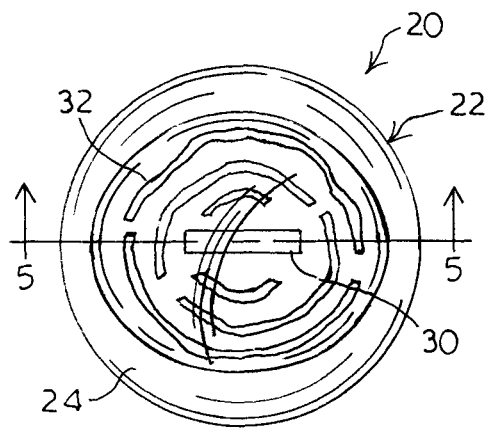
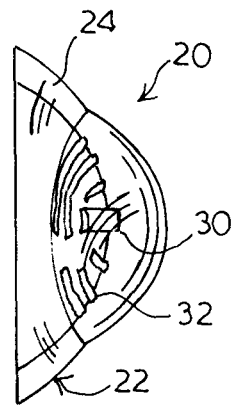
FIG. 2   FIG. 3
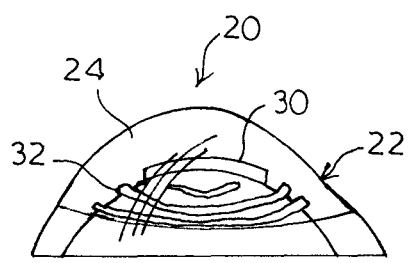
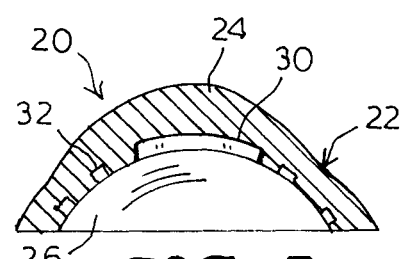
FIG. 4   FIG. 5
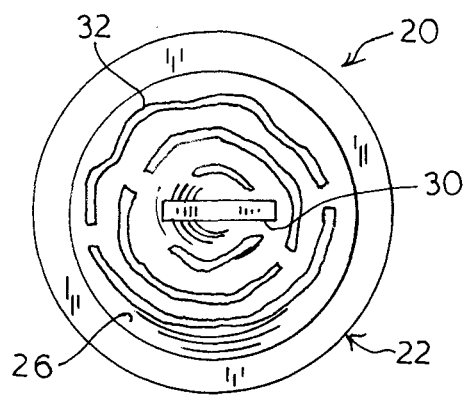
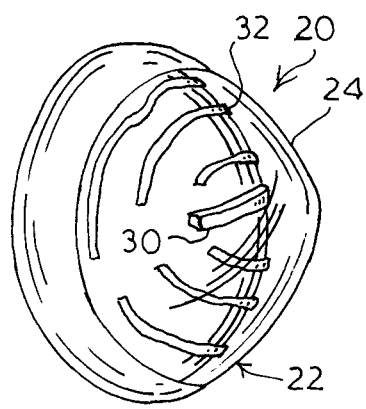
FIG. 6   FIG. 7

ARTIFICIAL EYE AND METHOD OF MANUFACTURE

BACKGROUND

This invention relates generally to artificial eyes, and more particularly to an artificial eye for use in taxidermy and a method for manufacturing the eye.

An artificial animal eye used in taxidermy is typically made from an eyepiece blank formed from transparent glass, crystal, plastic or other glass-like substrate. The conventional eyepiece blank used in taxidermy is semi-spherical and has a concave inner surface and a convex outer surface. Glass eyepieces are typically hand painted by artisans using variously colored glazes or vitreous glass enamels. Color is applied to the concave inner surface of the eyepiece to realistically simulate the natural elements and colors of an animal eye. For example, typical coloration of an artificial eye simulates a sclerotic capsule or base, pupil, iris, and cornea elements. The eyepiece is fired to fuse the color to the glass substrate.

Artificial eye construction requires significant artistic skill, time, anatomical knowledge, and experience to create realistic artificial eyes. However, conventional artificial eyes for taxidermy purposes tend to look unrealistic, since artificial eyes are expressionless and lack the intricate details characteristic of a natural eye.

For the foregoing reasons, there is a need for a new artificial eye and manufacturing method that results in a more realistic artificial eye for use in taxidermy. Ideally, the new artificial eye will have substantially the same natural coloration and appearance of the animal eye it represents.

SUMMARY

An artificial eye is provided, comprising a transparent cup-shaped body member having a substantially concave inner surface and a substantially convex outer surface. The body member includes a pupil portion at the center, a substantially annular iris portion abutting the peripheral edge of the pupil portion for defining a boundary between the pupil portion and the iris portion, and at least one groove formed in the concave inner surface of the iris portion of the body member. The grooves are visible through the iris portion for reflecting light through the body member.

BRIEF DESCRIPTION OF THE DRAWINGS

For a more complete understanding of the present invention, reference should now be had to the embodiments shown in the accompanying drawings and described below. In the drawings:

FIG. 2 is a front elevation view of a transparent eyepiece blank for use according to an embodiment of an artificial eye.

FIG. 3 is a right side elevation view of the transparent eyepiece blank as shown in FIG. 2.

FIG. 4 is a top plan view of the transparent eyepiece blank as shown in FIG. 2.

FIG. 5 is a longitudinal cross-section view of the transparent eyepiece blank taken along line 5-5 of FIG. 2.

FIG. 6 is a rear elevation view of the transparent eyepiece blank as shown in FIG. 2.

FIG. 7 is a perspective view of the transparent eyepiece blank as shown in FIG. 2.

DESCRIPTION

Certain terminology is used herein for convenience only and is not to be taken as a limitation on the invention. For example, words such as "upper," "lower," "left," "right," "horizontal," "vertical," "upward," and "downward" merely describe the configuration shown in the FIGs. Indeed, the components may be oriented in any direction and the terminology, therefore, should be understood as encompassing such variations unless specified otherwise.

As used herein, the term "paint" is a verb to describe a process for applying ink, paint, etc., to the surface of an eyepiece blank, but the term is intended as it is used herein to encompass painting, inking, printing, drawing, stenciling, stamping and other means which are useful for this purpose as would be recognized by one skilled in the art. Thus, "painting" is used similarly, but expressly includes inking, printing, including pad printing, stamping, and the like.

As used herein, the term "species" comprises any class or group of human, animal, bird, fish, reptile, amphibian, mammal, doll, or other type mannequin wherein an artificial eye is used.

Figure 1:
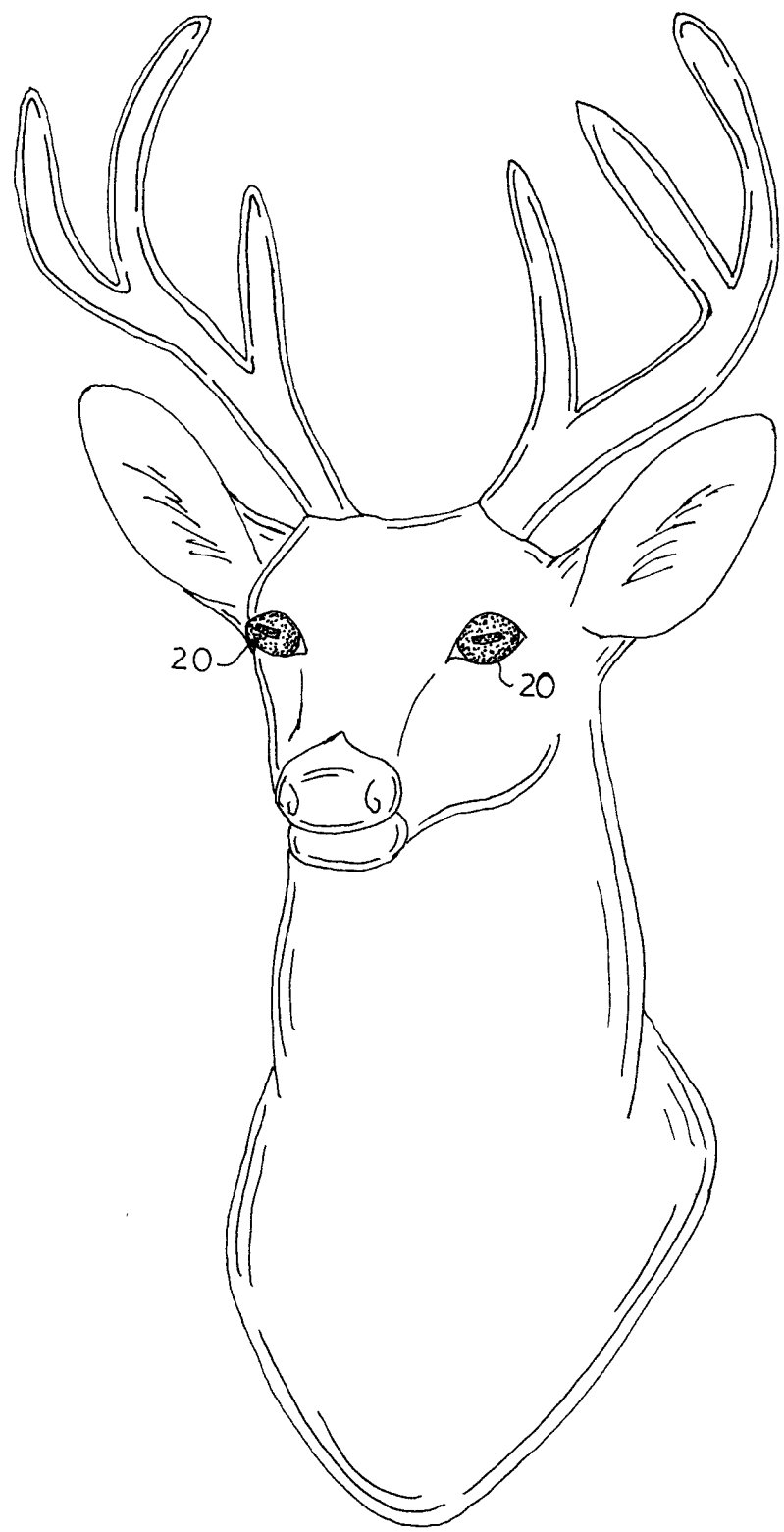
FIG. 1 is a perspective view of a mounted deer head including an embodiment of an artificial eye.

Referring now to the drawings, wherein like reference numerals designate corresponding or similar elements throughout the several views, an embodiment of an artificial eye is shown in FIG. 1 being positioned in eye sockets of a mounted deer head and are generally designated at 20.

It is understood that, although an artificial eye will be described in detail herein with reference to an exemplary embodiment for use as a deer eye in a taxidermy application, the artificial eye may be used in other artificial eye applications in taxidermy. As is known in the art, visible eye elements of different species vary by shape, color and size. For example, a deer has a differently shaped and differently colored visible eye than a snake or a fish; therefore, an artificial eye for a deer would have a different shape and color than an embodiment of an artificial eye for a snake or a fish. However, each species comprises several visible and individually recognizable elements. When producing artificial eyes, these elements of the eye must be artistically and accurately represented to properly simulate the natural eye of that species. The individual elements, determined by the size and the specific characteristics of the individual species being reproduced, must be properly depicted or simulated to produce the realism desired. In addition, artificial eyes are used in a wide variety of other applications such as, for example, dolls, toys, stuffed animals, mannequins, models, statues, fishing lures and the like, as well as prosthetic eyes for a human being. Accordingly, although the embodiments described herein are based upon the disclosed deer eye, it is understood that other types and sizes of artificial eyes used in taxidermy, as well as other applications in which a realistic or fanciful artificial eye is desired, are contemplated for the artificial eye described herein.

FIGS. 2-7 show an embodiment of an artificial deer eyepiece blank 22. The eyepiece blank 22 may be any size or material with no limitation. By way of example, the blank is a commercially available, manufactured eyepiece blank in the form of a semi-spherical shell made of transparent glass, crystal, plastic or the like. The blank has a smooth convex outer surface 24 and a concave inner surface 26. The outer surface 24 may be shaped aspherically (FIG. 3), or include a central raised portion 28 shaped to resemble the iris of the animal eye which it simulates. The concave inner surface 26 of the eyepiece blank 22 forms a slot 30 defining an elongated pupil area. It is understood that that artificial eyepieces having round or other shaped pupils may also be used in accordance with other embodiments of artificial eyes for other animals.

As shown in the FIGs., the artificial eye 20 is formed in its inner concave surface 26 with one or more grooves 32, such that the inner surface 26 of the eye surrounding the slot 30 defining the pupil area is scored by the one or more grooves. The grooves 32 are purposely made random and somewhat irregular in length, or "broken", and direction. In the embodiment shown, a plurality of laterally spaced irregular and circumferentially extending endless grooves 32 are provided. The length and direction of the grooves 32 may vary based on the artistic desires and skill of the artist, for example, being slightly curved or straight for portions along their length. The depth and width of the grooves 32 may also vary, being of diminishing dimensions at their ends, or more or less prominent as desired. In one embodiment, the grooves for a deer eye are from about 0.010 inches to about 0.020 inches wide, and about 0.025 inches to about 0.030 inches deep. At widths of less than about 0.010 inches, or depths less than about 0.025 inches, the visual effect created by the grooves 32 is minimized. At depths of greater than about 0.030 inches, the grooves become too visible through the eye, with the visual effect akin to a topographical map. Numerous methods and materials may be applied for forming the grooves 32 in the eyepiece blank 22.

Figure 8:
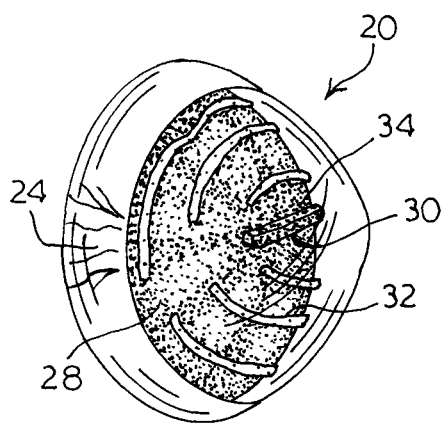
FIG. 8 is a perspective view of an embodiment of an artificial eye for use in a deer mount as shown in FIG. 1.
Figure 9:
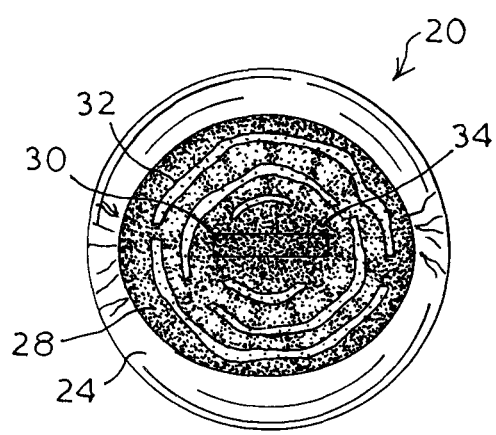
FIG. 9 is a front elevation view of the artificial eye as shown in FIG. 8.
Figure 10:
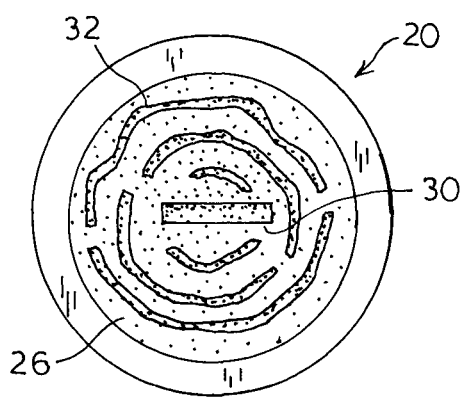
FIG. 10 is a rear elevation view of the artificial eye as shown in FIG. 8.

Referring to FIGS. 8-10, the eyepiece blank 22 is shown as colored on the concave inner surface 26 by applying one or more coating layers of appropriate colors in a manner recognized in the taxidermy art, or by practitioners familiar with artificial or glass eyes, to realistically simulate the colors and appearance of a natural eye. Natural coloration of a glass eyepiece blank may be achieved through the application of colored glazes to selected areas on the concave inner surface of the eyepiece blank. Conventional low-fire leaded or non-leaded glass enamel glazes may be used to achieve natural eye coloration and texture. Various application methods, including air brushing, may be used to apply the different colors and textures to the selected areas of the eyepiece blank 22. Layers of coloration which overlie each other will have cumulative color value, with the relative color value of the parts of the eye being altered at will. In one embodiment, a layer of coloration is applied in the grooves 32 and then a portion of the coloration removed, such as by wiping. A second cover layer of coloration is next applied. This technique provides a visual effect in the grooves 32 that differs form the visual effect of the surrounding area.

After the coloration glazes are allowed to dry thoroughly, the eyepiece blank 22 is fired in a kiln to causing the glazes to fuse with the glass. The artificial eye 20 is then allowed to cool completely. As is known in the art, there may several steps involving the addition of coloration to the eyepiece blank 22 followed by firing. The completed artificial eye 20, with grooves 32 integrally formed in the inner concave surface 26 thereof, is then ready for use in a taxidermy mount. Note that wherein the eyepiece blank 22 is to be made of transparent materials other than glass, such as plastic, the coloration methods would be replaced by those appropriate for applying color to transparent plastic.

The visible elements of an eye, located in the front of the eye, provide the variations that uniquely identify a particular species. Depending on the species, the visible or recognizable elements of an eye generally include elements such as a sclera, iris, pupil and cornea. The base portion of the eye corresponds to the sclera. The sclera is an opaque dense outer coat enclosing the entire eyeball except the part of the eyeball covered by the cornea. The sclera or sclerotic capsule may vary in size, shape and color for each species. A large portion of the sclera is fitted into the eye cavity and thus not externally visible.

In the present embodiment of an artificial eye for a deer, brown coloration is applied to a central iris portion 28 of the concave inner surface 26 of the eyepiece blank 22. The iris may be flecked with a lighter shade of brown or gold. The pupil 34 of a deer eye is a substantially oval shape, and is a void and having no color. A deer pupil does have a blackish blue hue due to reflection of the retina behind the pupil. Otherwise, the pupil has no noticeable details within that need to be reproduced in an artificial eye. Accordingly, in this embodiment, all that is needed is a solid, opaque oval shape of blackish blue coloration oriented along the slot 30 in the inner surface 26 of the eyepiece blank 22. A band of whitish coloration is applied on the concave inner surface of the eyepiece in the area of the sclera located between the central iris portion 28 and the outer circumferential edge of the eyepiece blank 22.

It is understood that the color, size and shape of the pupil corresponds to the specific species being simulated. For example, the pupil for a deer eye will be oblong in shape whereas the pupil for a bird eye will usually be round, and the pupil for a cat eye will be a slit shape. The colored iris surrounds the pupil. There may also be dark shading around the pupil and a dark shading at the edge of the iris called the limbus band.

In an alternative, a combination of colored glass and painted inner surface is used to create a life-like artificial eye.

The embodiment of the artificial eye and method of manufacture described herein provides a realistic artificial eye 20 with a natural appearance of depth and liquidity. Portions of the painted image of the artificial eye 20, particularly the iris 28, are translucent to allow light to penetrate. While not intending to be bound to any particular theory, it is believed the magnifying effect of the glass, or other transparent substrate, upon the grooves 32; the refraction of light rays from the angularly disposed surfaces defining the grooves 32; and the diffusion of light rays due to the plurality of lines produced by the grooves 32, all combine to create this unique visual effect. Since the grooves 32 are disposed behind the iris 28 of the artificial eye 20, the effect is to provide depth and liquidity in the iris that radiates from and surrounds the pupil. The effect may also include a gradual shading of color from a light field immediately surrounding the pupil 34 to the dark ring on the edge of the iris 28. Because of the irregular character of the grooves 32 and the consequent indefinite defining lines, and the distortion of lines of vision through the artificial eye 20, the iris 28 and pupil 34 appear to lose precise contour and slightly dilate or contract according to the changing angle from which the observation is made. As the point of observation changes, the refraction and diffusion of light causes a marked apparent difference in the size and contour of the iris 28 and pupil 34 so that an almost life-like appearance is secured.

Although the present invention has been shown and described in considerable detail with respect to only a few exemplary embodiments thereof, it should be understood by those skilled in the art that we do not intend to limit the invention to the embodiments since various modifications, omissions and additions may be made to the disclosed embodiments without materially departing from the novel teachings and advantages of the invention, particularly in light of the foregoing teachings. For example, the artificial eye described herein may also be adapted for taxidermy use for the eyes of other animals, and has broader applications for use in such things as dolls, toys and stuffed animals, mannequins, models, statues, fishing lures and any other application in which a realistic or fanciful artificial eye is desired, including prosthetic eyes for a human being. Accordingly, we intend to cover all such modifications, omission, additions and equivalents as may be included within the spirit and scope of the invention as defined by the following claims. In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures.

What is claimed is:

1. An artificial eye, comprising:
    a cup-shaped transparent body member having a substantially continuous concave inner surface and a substantially aspherical convex outer surface, the body member including:
    a pupil portion aligned under center of the aspherical convex outer surface, wherein the pupil portion is defined by a slot formed in the continuous concave inner surface of the body member, wherein the slot extends outwardly from the continuous concave inner surface towards the aspherical convex outer surface;
    a substantially annular iris portion abutting the peripheral edge of the pupil portion for defining a boundary between the pupil portion and the iris portion; and
    a plurality of spaced discontinuous grooves formed in the continuous concave inner surface of the iris portion of the body member, each groove of the plurality of grooves being straight or curvilinear in different directions along the length of the groove to provide the artificial eye with a natural appearance of depth and liquidity when painted, wherein each groove extends outwardly from the continuous concave inner surface towards the aspherical convex outer surface, wherein the grooves are visibly magnified through the iris portion for refraction of light rays from angularly disposed surfaces defining the grooves in the continuous concave inner surface and diffusion of light rays through the transparent body member.

2. An artificial eye as recited in claim 1, wherein the plurality of grooves are regularly spaced.

3. An artificial eye as recited in claim 1, wherein the body member is formed from at least one of glass or a combination of glass and at least one of crystal or plastic.

4. An artificial eye as recited in claim 1, further comprising a coating layer of color applied to the concave inner surface for simulating the coloring of the iris portion.

5. An artificial eye as recited in claim 4, wherein the layer of color is translucent.

6. An artificial eye as recited in claim 5, wherein the layer of color is in a form which substantially resembles an eye.

7. An artificial eye as recited in claim 1, wherein the body member further comprises a sclera portion between iris portion and the peripheral edge of the body member.

8. An artificial eye of claim 1, wherein said artificial eye is mounted to a form used in taxidermy.

9. An artificial eye as recited in claim 1, wherein the pupil portion is at least one of round, elongated, oblong, or a slit shape.

10. An artificial eye as recited in claim 1, wherein the plurality of spaced discontinuous grooves are irregularly spaced around a circumference of the iris portion of the body member.

* * * * *